US00PP25740P3

(12) United States Plant Patent
Sparks

(10) Patent No.: US PP25,740 P3
(45) Date of Patent: Jul. 28, 2015

(54) PECAN TREE NAMED 'TREADWELL'

(50) Latin Name: *Carya illinoinensis*
Varietal Denomination: Treadwell

(71) Applicant: University of Georgia Research Foundation, Inc., Athens, GA (US)

(72) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 109 days.

(21) Appl. No.: 13/987,384

(22) Filed: Jul. 19, 2013

(65) Prior Publication Data

US 2015/0026848 P1 Jan. 22, 2015

(51) Int. Cl.
*A01H 5/10* (2006.01)

(52) U.S. Cl.
USPC ..... Plt./153

(58) Field of Classification Search
USPC ..... Plt./153
See application file for complete search history.

*Primary Examiner* — Anne Grunberg
(74) *Attorney, Agent, or Firm* — Klarquist Sparkman, LLP

(57) ABSTRACT

A pecan tree distinguished by the following unique combination of characteristics: high precociousness and prolificacy, consistent production (if fruit thinned), early nut maturity, large nut size that produces mammoth halves, unusual high percentage kernel, exceptional kernel color, no kernel speckling has been observed, high resistance to N scorch, black pecan aphid, pecan leaf scorch mite, and good resistance to scab fungus.

5 Drawing Sheets

Latin name of the genus and species of the plant: *Carya illinoinensis.*

Variety denomination: 'Treadwell'.

BACKGROUND OF THE INVENTION

The present invention relates to a new and distinct variety of pecan tree named 'Treadwell.' My new tree can be used in gardens or for commercial production of pecan nuts. This new tree was selected from seedlings grown from controlled pollination at the University of Georgia Horticulture Farm in Watkinsville, Ga., in 1989. The 'Treadwell' selection resulted from crossing 'Wichita' (unpatented) as the seed parent with 'Pawnee' (unpatented) as the pollen parent. The resulting tree was selected when growing in a cultivated area at Watkinsville, Ga.

BRIEF SUMMARY OF THE INVENTION

'Treadwell' is distinguished from other pecan varieties known to the inventor due to the following unique combination of characteristics: high precociousness and prolificacy, consistent production (if fruit thinned), early nut maturity, large nut size that produces mammoth halves, unusual high percentage kernel, exceptional kernel color, immunity to kernel speckling, high resistance to N scorch, black pecan aphid, pecan leaf scorch mite, and good resistance to scab fungus.

Asexual reproduction of 'Treadwell' by grafting, (top working) onto 'Desirable' (unpatented) pecan trees in 2002 and 2007 at locations in Leary, Ga. and Albany, Ga., respectively, was performed in order to evaluate these trees. Asexual propagation of 'Treadwell' pecan trees has also been performed at other locations in Georgia. Asexual reproduction of 'Treadwell' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

The colors of an illustration of this type may vary with lighting and other conditions. Therefore, color characteristics of this new variety should be determined with reference to the observations described herein, rather than from these illustrations alone.

DETAILED DESCRIPTION

Botanical

The following detailed description of 'Treadwell' is based on observations of the original tree growing in Watkinsville, Ga. and of asexually reproduced progeny growing in Albany, Ga. and Leary, Ga.

Varietal name: 'Treadwell'.

Parentage:

*Seed parent*.—'Wichita'.

*Pollen parent*.—'Pawnee'.

Tree:

*Overall shape*.—Moderately spreading, height to width ratio is about 1:1. Tree stature is short and about one half of 'Byrd' and 'Cunard'.

*Vigor*.—Vigorous, precocious, 'Treadwell' fruited the second year after grafting (top working) onto 'Desirable' trees, and has done so in subsequent years. Original tree fruited 10 years from seed.

*Height*.—Of original tree, about 11 meters.

*Width*.—Of original tree, about 11 meters.

*Trunk*.—Of original tree (measured ½ meter above ground level) about 0.8 meters circumference.

*Trunk bark texture*.—Scaly with tree maturity.

*Trunk bark color*.—Grey (RHS 202B).

*Patches*.—Trunk has no markings.

*Branch color*.—Branch shoots in woody stage are Grey-brown (RHS 199A) in color, with Grey-brown lenticels (RHS 199D) that are elongated and about 1 mm long by 0.05 mm wide.

*Internodes*.—Average internode length is about 1.3 cm, between the $3^{rd}$ and $4^{th}$ leaf on a shoot.

*Bearing*.—Consistent production of fruit if thinned.

*Disease and insect resistance*.—High resistance to N scorch. High resistance to black pecan aphid *Melanocallis caryaefoliae* (Davis). High resistance to pecan leaf scorch mite *Eotetranychus hicorire* (McGregor). Good resistance, but not immunity, to scab *Fusicladosporium effusum* (G. Winters) Partridge & Morgan-Jones.

Figure 2:
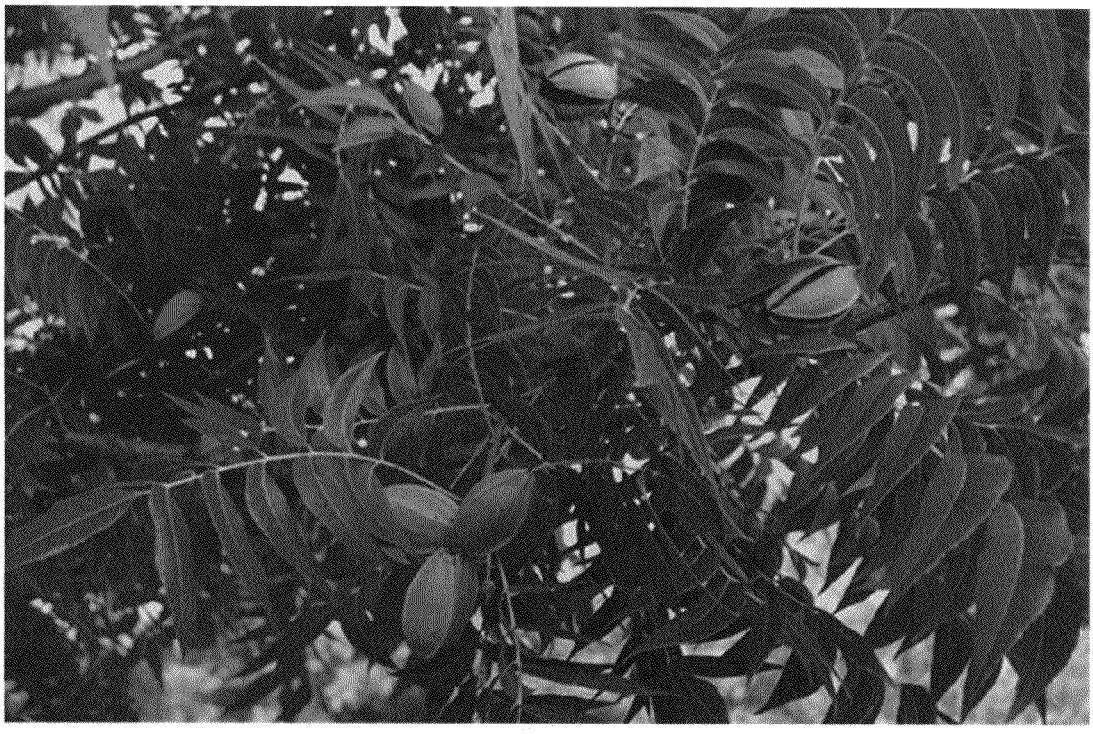
FIG. 2 is a photograph showing the leaves of 'Treadwell'.

Leaves: The mature leaf is odd pinnate compound, deciduous with leaflets having a dark green upper surface and a lighter green lower surface. Each mature leaf has from 13 to 17 leaflets. Leaf architecture is mixed on the same shoot. Some leaflets droop slightly whereas on other leaves drooping is not present, opposite leaflets are oriented at 180° relative to the rachis (see FIG. 2).

*Size of mature leaf* (*fourth leaf from base*).—14.4 cm long, 19.2 cm wide.

*Peduncle*.—Oval in cross-section, tan in color (RHS 199B). The length of the peduncle of the fourth leaf from the base is about 4.3 cm. The diameter of the peduncle of the fourth leaf from the base is about 2.7 mm.

*Leaflet*.—Size and shape: Fourth leaflet on fourth leaf from base 9.7 cm long by 3.0 cm wide. Falcate in shape. Base oblique. Margin serrate. Convolution of leaflets is absent on basal leaves, but increases from basal to apical leaves on vigorous shoots. Leaflets are non convoluted on mature trees. Texture: Smooth. Sheen: Glossy. Petiole: Sessile. Margin: Serrate. Tip shape: Acuminate and narrow. Leaflet color: Upper leaf surface: Forest green (RHS 137A). Lower leaf surface: Green (RHS 138A). Pubescence: Upper leaf surface is not pubescent. Lower surface is pubescent. The length, width and other measurements were obtained from observations of a typical leaf.

Inflorescence:

*General*.—The 'Treadwell' pecan is monoecious, anemophilous, and protandrous.

*Flowers*.—Pistil flowers are borne on a determinate spike, with staminate flowers borne on a determinate pendulous catkin. Three-five individual pistillate flowers per spike, borne alternately on terminally-positioned spikes. The pistillate flower is symmetrical with no stamens or petals. The pedicels are sessile. The staminate or catkin length is 84 mm and width is 6 mm. The staminate color is Green (RHS 144B) with gold pollen (RHS 3A). The involucre size, which includes the stigma, is 11.7 mm long by 2.8 mm wide. The flower has one pistil with an oxblood (RHS 61 A) stigma. The flower has four bracts, which are green (RHS 144A), lanceolate, 4.4 mm long by 0.5 mm wide and are fused at the bases, forming a copular involucre.

Fruit: Mature fruit is dehiscent.

Figure 1:
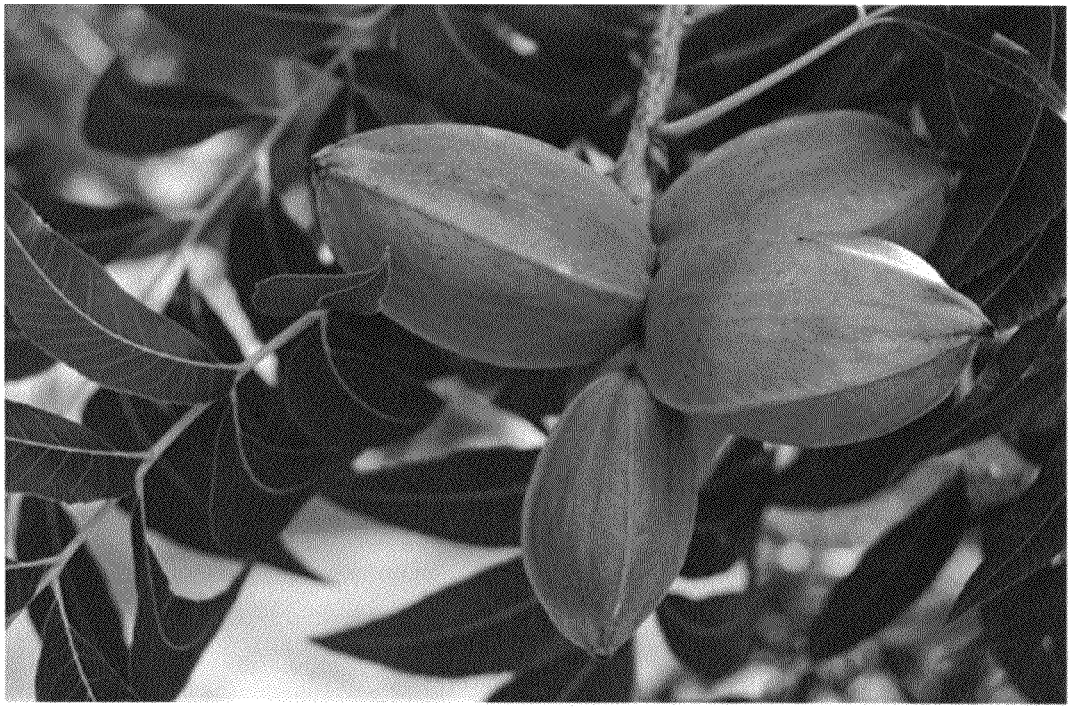
FIG. 1 is a photograph showing a fruit cluster of 'Treadwell' pecans.
Figure 3:
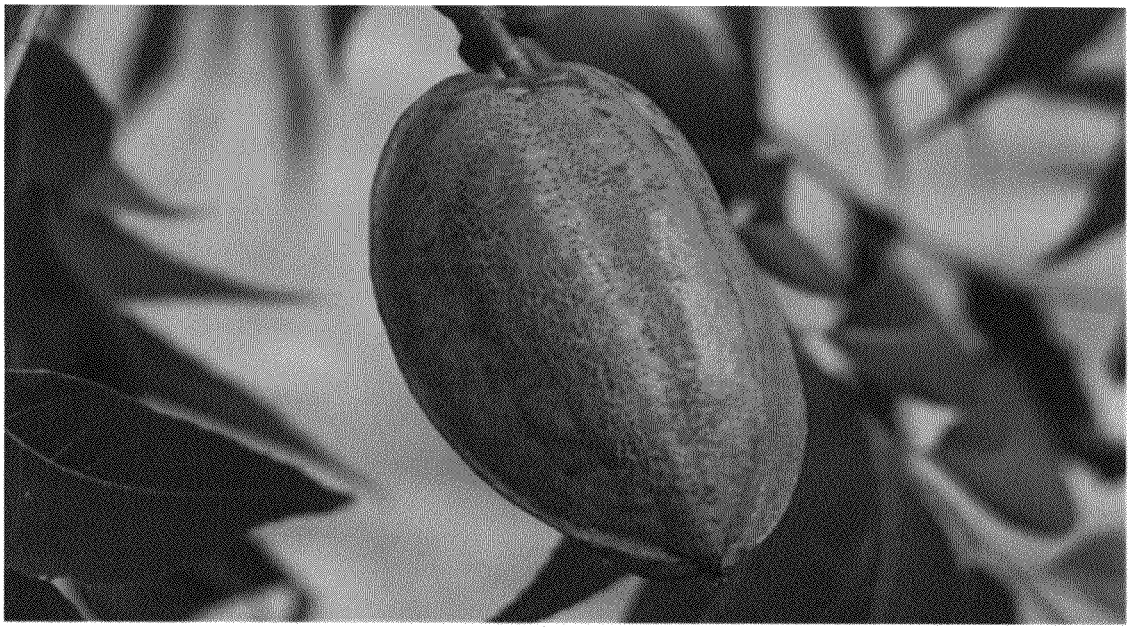
FIG. 3 is a photograph showing the characteristic russet shuck of 'Treadwell'.
Figure 4:
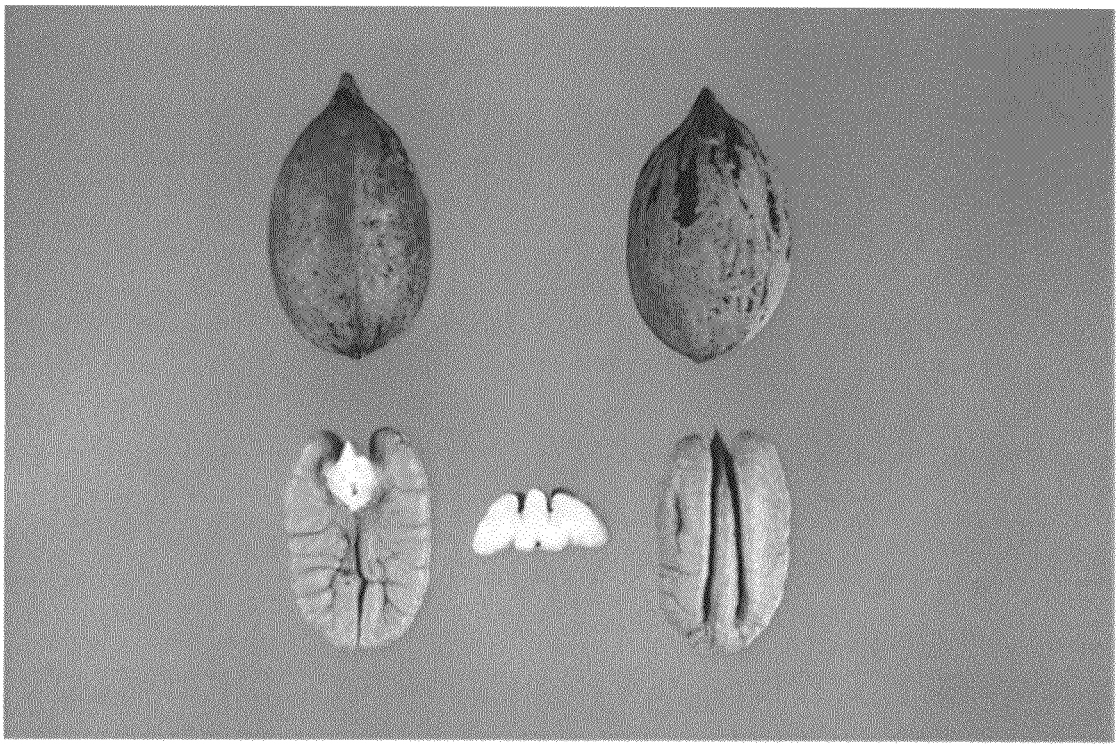
FIG. 4 is a photograph showing nut shape and kernel characteristics of 'Treadwell'. From left to right in FIG. 4: the top views depict the suture side and the non-suture side of the nut; and the bottom views, from left to right, depict the ventral side of the kernel, the kernel in cross-section (dorsal side up), and the dorsal side of the kernel.
Figure 5:
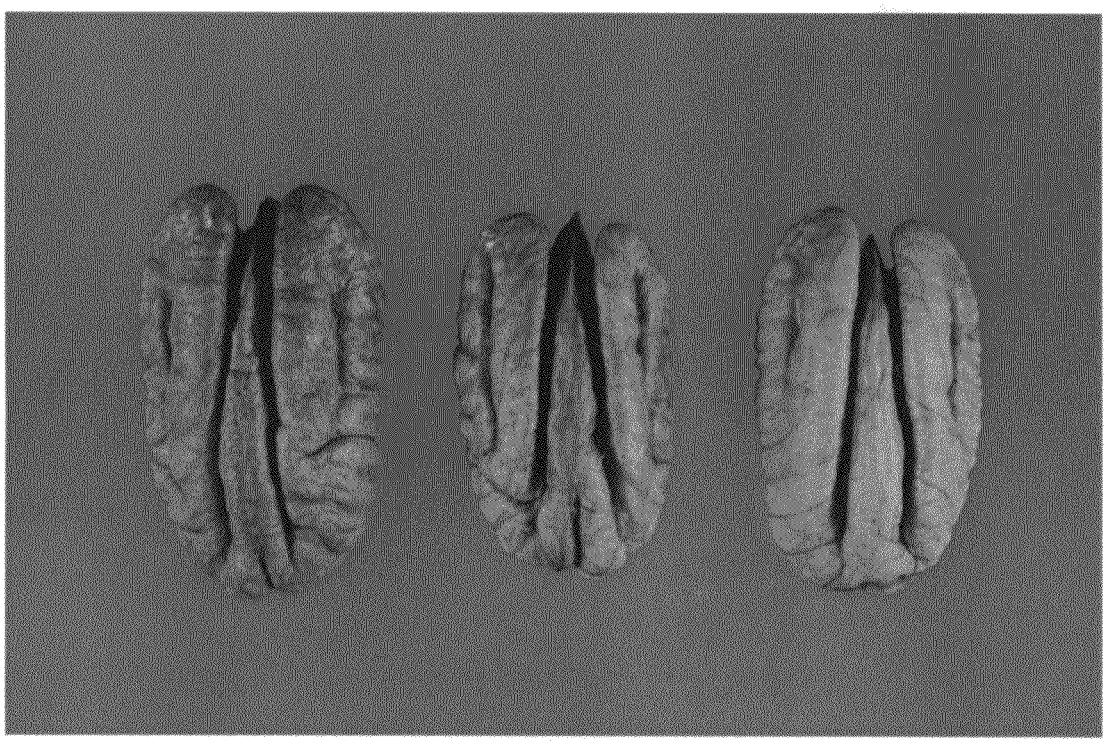
FIG. 5 is a photograph showing kernel and color of 'Cunard,' 'Byrd,' and 'Treadwell', with 'Cunard' (now U.S. Plant Pat. No. 24,373) being on the left, 'Byrd' (U.S. Plant Pat. No. 20,867) being in the middle and 'Treadwell' being on the right in FIG. 5.

*Shuck*.—Green (RHS 144B), russet with maturity (see FIG. 3). The shuck sutures are slightly winged (see FIG. 1) and the shuck surface is not indented. 'Treadwell' produces a low percentage (<5%) of undersized fruit ("green pops") in which the kernel does not develop and the shuck fails to dehisce.

*Fruit split during water stage*.—Not observed to be a problem.

*Shuck decline*.—Shuck dieback during kernel formation has not been observed to be a problem.

Nuts: Observations from a limited number of typical nuts from several growing seasons in Watkinsville, Ga.

*Size*.—Large, length about 40 mm, width about 21.6 mm (width measurement taken midway along the length of the nut and across sutures); length to width ratio about 1.9. Nut flatness (ratio of width across sutures to width between sutures) is about 1.0.

*Form*.—Oblong with a blunt (obtuse) base and a round cross section, apex shape is cuspidate to cuspidate asymmetric, with a grooved apex.

*Sutures*.—Non-elevated.

*Dorsal grooves*.—Narrow and shallow, thereby increasing the percentage kernel in the nut.

*Weight*.—8.7 grams per nut (non-limiting soil moisture).

*Cluster size*.—About 2.7 fruits per cluster.

*Shell texture*.—No ridges.

*Shell thickness*.—Thin, 0.73 mm.

*Kernel color*.—Good color, Greyed-orange (RHS 165B).

*Kernel coat*.—No speckling has been observed.

*Kernel percentage of nut*.—About 64 percent (non limiting soil moisture).

*Nut maturity*.—September 24th. Later than 'Byrd' by about 3 days.

*Harvestability*.—Suitable for machine harvest.

*Cracking/shelling ability*.—Cracks exceptionally well, percentage of kernels with intact halves is high. Typically, less than five percent of chipped or broken kernels were observed.

COMPARISONS TO OTHER VARIETIES

The form of 'Treadwell' trees is moderately spreading and similar to both parents and is shorter in stature than 'Byrd', 'Cunard', 'Morrill' (U.S. Plant Pat. No. 23,335) and most other pecan varieties. The timing of bud break of 'Treadwell' is similar to 'Byrd' and 'Cunard' and earlier than 'Morrill', 'Stuart' (unpatented), and many pecan varieties. Thus, 'Treadwell' is somewhat more susceptible to late-spring freezes in Georgia than 'Stuart' and 'Morrill'. The leaves of 'Treadwell' are dark green and similar to both parents. Leaflet orientation of 'Treadwell' leaves is unlike 'Huffman' (soon to be patent pending), that is, leaf architecture is mixed on the same shoot. Some leaflets droop slightly whereas on other leaves drooping is not present, opposite leaflets are oriented at 180° as in the parent 'Pawnee'. Leaflets are non convoluted in 'Treadwell' except on vigorous shoots. The stigmatic surface of 'Treadwell' is oxblood (RHS 61A), similar to the oxblood color of parent 'Pawnee' and in contrast to the green surface of parent 'Wichita' (unpatented). In the comparison tables below, 'Cheyenne', 'Elliott' and 'Schley' are unpatented varieties.

TABLE 1

Approximate periods of pollen shedding and stigma receptivity for 'Treadwell' and selected other varieties in May.

| | Date | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Protandrous varieties | | | | | | | | | | | | | | | | | | |
| Cheyenne | | | | | | | | | | | | | ..... | | | | | |
| Desirable | | | | | | | | | | | | | | ..... | | | | |
| Treadwell | | | | | | | | | | | | | | ..... | | | | |
| Protogynous varieties | | | | | | | | | | | | | | | | | | |
| Elliott | | | | | | ..... | | | | | | | | | | | | |
| Schley | | | | | | ..... | | | | | | | | | | | | |
| Stuart | | | | | | ..... | | | | | | | | | | | | |

..... = Period of stigma receptivity.
___ = Period of pollen shedding.

Tables 2 and 3 below compare the characteristics of nuts from 'Treadwell' with nuts of other pecan varieties.

TABLE 3

Nut characteristics of 'Morrill,' 'Cunard,' and 'Treadwell,' Albany, Georgia.

| Variety | Lbs./tree | Nuts/lb. (no.) | Kernel (%) |
|---|---|---|---|
| 'Morrill' | 27 a | 45 a | 66.2 b |
| 'Cunard'[z] | 32 a | 40 a | 60.9 a |
| 'Treadwell'[z] | 34 a | 52 b | 61.3 a |

Means followed by the same letter within a column are not statistically different, $P \leq 0.05$.
Greater nut size and percentage kernel in Albany, Georgia as compared to Watkinsville, Georgia (Table 2) believed due to better irrigation and probably higher temperatures in Albany, Georgia. Soil water was non-limiting at Albany, but not at Watkinsville.
[z]'Cunard and 'Treadwell' were fruit thinned as needed. About 50% of the fruit was removed. 'Morrill' was not fruit thinned.

Pecan nuts of large size that mature relatively early command a premium price. The price per pound normally declines as the harvest becomes later. Consequently, cultivars that exhibit early maturity at harvest are commercially important. The color of a kernel's seed coat (lighter is preferred), and the percentage kernel of the nut also affects the selling price of pecans. Nut maturity of 'Treadwell' is early, similar to 'Byrd' and 'Cunard', slightly later than 'Pawnee' and 21 days before 'Desirable'. 'Desirable' (unpatented) is believed to be the leading cultivar now being planted in new orchards in Georgia.

As can be seen from Tables 2 and 3, the nut size of 'Treadwell' nuts is similar to that of 'Pawnee' and 'Byrd' and smaller than 'Cunard' and 'Morrill'. However, the nut length is shorter in the case of 'Treadwell' nuts than 'Byrd' nuts and the nut shape differs. As indicated by the length to width ratio, 'Treadwell' nuts are less oblong than 'Pawnee' nuts. In cross-section, 'Treadwell' and 'Pawnee' nuts are near round (flatness ratio 0.97 and 0.96, respectively) while 'Byrd' nuts are flatter on the suture side than the non-suture side. Referring to Table 2, the shell thickness of 'Treadwell' is similar to 'Pawnee' but thicker than 'Byrd'. All three have unusually thin shells, which accounts, in part, for their high percentage kernel. However, the percentage kernel of 'Treadwell' and 'Cunard' nuts is substantially lower than nuts of 'Byrd', which has a thinner shell. The morphology of the dorsal grooves also affects percentage kernel. 'Morrill' has exceptional narrow and shallow grooves resulting in a very high percentage kernel. The percentage kernel is a direct function of the shell thickness and the percentage of the shell cavity filled with the kernel.

TABLE 2

Comparison of nut characteristics of 'Byrd,' 'Pawnee,' 'Morrill,' 'Cunard,' 'Treadwell,' and 'Stuart pecan varieties, Watkinsville, Georgia.

| Variety | Wt./nut (g) | Nuts/lb (no.) | Nut length (mm) | Length/width[z] | Nut Flatness ratio[y] | Shell thickness (mm) | Kernel (%) | Nut Maturity date[x] |
|---|---|---|---|---|---|---|---|---|
| 'Byrd' | 7.7 bc | 60 ab | 42.5 b | 1.87 c | 1.04 b | 0.65 c | 63.0 b | 21 de |
| 'Pawnee' | 7.6 c | 61 a | 41.9 bc | 1.95 b | 0.96 d | 0.77 b | 59.5 c | 20 e |
| 'Morrill' | 8.5 b | 54 bc | 47.1 a | 2.01 b | 1.11 a | 0.72 bc | 66.2 a | 33 b |
| 'Cunard' | 9.4 a | 48 c | 47.7 a | 2.13 a | 1.01 c | 0.73 b | 61.8 bc | 26 c |
| 'Treadwell' | 7.5 c | 61 a | 40.1 cd | 1.86 c | 0.97 d | 0.73 b | 59.8 c | 24 cd |
| 'Stuart' | 7.5 c | 61 a | 38.9 d | 1.69 d | 1.01 c | 0.90 a | 47.7 d | 40 a |

Means followed by the same letter within a column are not statistically different, $P \leq 0.05$.
[z]Length to width ratio = nut length divided by width. Width was measured midway the length of the nut and across sutures.
[y]Nut flatness ratio = ratio of nut width across sutures to width between sutures. Measurements were made midway the length of the nut.
[x]Date when shuck dehiscence had occurred on 50% of the fruit, from September 1.

The percentage kernel of 'Treadwell' nuts, as can be seen from Tables 2 and 3, is high, especially when soil moisture is not limiting.

Under stress, primarily fruiting stress, when 'Pawnee' cultivar pecan trees are grown in humid southeastern United States, the kernel seed coats of nuts can develop conspicuous and unattractive dark spots. This speckling reduces the marketability of these nuts. Speckling has not been observed to be a problem of 'Treadwell' nuts grown in Georgia. Kernel color is outstanding and superior to the other two early maturing varieties, 'Byrd' and 'Cunard'. In addition, unlike the 'Treadwell' cultivar, during a heavy "on" nut production year for 'Pawnee' trees growing in Georgia, kernel development is relatively poor, resulting in a high percentage of the nuts being unmarketable or of reduced value.

TABLE 4

Precocity of 'Byrd', 'Cunard', 'Treadwell', 'Morrill', 'Desirable', 'Huffman', and 'Stuart'.

| Variety | Years to initial fruiting [z] |
|---|---|
| Cunard | 2 |
| Byrd | 3 |
| Treadwell | 3 |
| Morrill | 4 |
| Desirable | 4 |
| Huffman | 6 |
| Stuart | >6 |

[z] Years from planting nursery trees.

Table 5 below compares the fruiting characteristics of 'Byrd,' 'Treadwell,' 'Huffman,' 'Cunard,' and 'Morrill' varieties.

TABLE 5

Fruiting characteristics of 'Byrd' and 'Morrill', Albany, Georgia.

| Variety | Years to fruiting (no.) | Years until alternate bearing[z] (no.) |
|---|---|---|
| 'Byrd' | 2 | 3 |
| 'Treadwell' | 2 | 3 |
| 'Huffman' | 2 | >6 |
| 'Cunard' | 2 | 10 |
| 'Morrill' | 2 | >9 |

[z]Years after top working mature trees to the respective cultivar.

TABLE 6

Production and nut characteristics of six year old pecan trees of 'Byrd', 'Cunard', 'Treadwell', and 'Cape Fear' (unpatented), Leary, Ga. [z]

| Variety | Yield (lb/tree) | Nuts/lb. (no.) | Kernel (%) |
|---|---|---|---|
| Byrd | 13.2 a | 48.2 bc | 63.7 a |
| Cunard | 11.8 a | 41.4 a | 64.3 a |
| Treadwell | 6.1 b | 48.6 c | 64.2 a |
| Cape Fear | 2.5 c | 46.8 b | 56.2 b |

Means followed by the same letter are not statistically different, $P \leq 0.05$ n = 26.

[z] Nut weight and kernel percentage are higher and nuts per pound is lower than in Table 2 because of better irrigation.

As apparent from Table 4, the 'Treadwell' variety is precocious, similar to 'Byrd' and second only to 'Cunard'. Its high precocious results in early alternate bearing (Table 5), indicating that fruit load will have to be controlled by mechanical fruit thinning. During the third year of fruiting, Treadwell is about 2.5 times more prolific than the standard 'Cape Fear' but about 2.0 times less than 'Byrd' and 'Cunard' (Table 6). The smaller cluster size of 'Treadwell' than that of 'Byrd' and 'Cunard' (Table 7) may account in part for its lower prolificacy but the primary factor is its short tree stature which can be partially compensated by increasing the tree density per acre. 'Treadwell's' short stature makes it suited to high density planting which contrasts with 'Byrd', 'Cunard', 'Huffman', and 'Morrill'. However, the difference in prolificacy as a young tree is not a factor as a mature tree. As a mature tree, prolificacy of 'Treadwell' is equal to the more precocious 'Cunard' (Table 3). This occurs because both cultivars and 'Byrd' produce more nuts as a mature tree than they can adequately mature or "fill". This problem is universal with precocity and prolific pecan cultivars. The problem is circumvented by mechanically removing or thinning the excess fruit.

TABLE 7

Fruit cluster size of 'Byrd,' 'Desirable,' 'Morrill,' 'Pawnee,' 'Cunard,' and 'Treadwell,' Watkinsville, Georgia.

| Variety | Fruit/cluster (no.) |
|---|---|
| 'Byrd' | 3.1 ab |
| 'Desirable' | 1.5 d |
| 'Morrill' | 2.7 bc |
| 'Pawnee' | 3.1 ab |
| 'Cunard' | 3.4 a |
| 'Treadwell' | 2.7 bc |
| 'Huffman' | 1.7 d |

Means followed by the same letter are not statistically different, $P \leq 0.05$.

Table 8 below compares N scorch, pecan leaf scorch mite, and leaf scab susceptibility of 'Byrd,' 'Morrill,' 'Cunard,' 'Treadwell,' and 'Desirable.' In addition, 'Pawnee' has been observed to be more susceptible to scab disease than 'Treadwell' when grown in Georgia. 'Wichita', when grown in Georgia's humid climate, is highly susceptible to scab fungus.

TABLE 8

N scorch, pecan leaf scorch mite, and leaf scab susceptibility of 'Byrd,' 'Morrill,' 'Cunard,' and 'Treadwell'.

| | | Pecan leaf | Leaf Scab[z] | |
|---|---|---|---|---|
| Variety | N scorch[x] | scorch mite[y] | Leary, 2009 | Watkinsville, 2010 |
| 'Byrd' | 1.2 a | 1.1 b | 1.0 a | 1.4 b |
| 'Morrill' | 1.5 a | 1.2 b | 1.3 a | 2.0 b |
| 'Cunard' | 1.1 a | 2.2 c | 1.3 a | 1.8 b |
| 'Treadwell' | 1.0 a | 2.7 a | 1.3 a | 1.6 b |

Means followed by the same letter are not statistically different, $P \leq 0.05$, n = 19.

[x]1 = no scorch; 2 = <1% of leaves with scorch; 3 = 2 to 20%; 4 = 21 to 40%; 5 = ≥ 41%.

[y]1 = no damage; 2 = trace; 3 = multiple lesions; 4 = minor defoliation; 5 = severe defoliation.

[z]1 = no scab lesions, 2 = occasional lesion on leaf, less than 1% of leaves with lesions, 3 = lesions scant on 2 to 10% of leaves, 4 = lesions widespread but no leaf distortion, 5 = lesions widespread and severe leaf distortion.

Table 9 below compares the black pecan aphid resistance of 'Byrd,' 'Morrill,' 'Cunard,' 'Huffman', 'Treadwell,' and 'Sumner.'

TABLE 9

Black pecan aphid susceptibility of 'Byrd,' 'Morrill,' 'Cunard,' 'Huffman' 'Treadwell,' and 'Sumner,' Leary, Georgia.

| Variety | Black pecan aphid [x] |
|---|---|
| 'Byrd' | 1.9 a |
| 'Morrill' | 1.9 a |

TABLE 9-continued

Black pecan aphid susceptibility of 'Byrd,' 'Morrill,' 'Cunard,' 'Huffman' 'Treadwell,' and 'Sumner,' Leary, Georgia.

| Variety | Black pecan aphid [x] |
|---|---|
| 'Cunard' | 1.9 a |
| 'Huffman' | 1.4 b |
| 'Treadwell' | 2.1 a |
| 'Sumner' | 1.8 a |

Means followed by the same letter are not statistically different, $P \leq 0.05$.

[x] 1 = no injury; 2 = <1% of leaves with injury; 3 = 1-10% of leaves with injury; 4 = 11-50% of leaves with injury; 5 = >50% of leaves with injury and partial defoliation.

Under the humid growing conditions in Georgia, the fruit is highly susceptible to splitting during the "water stage" (liquid endosperm stage) of fruit development. Fruit split can occur following rain and accompanying high humidity in early August in Georgia. Cultivars with positive nut qualities have become less desirable for growing in Georgia because of the susceptibility to scab fungus and water splitting. Water split has not been observed to be a problem in 'Treadwell'.

The 'Treadwell' pecan tree is therefore an improved new and distinct pecan.

I claim:

1. A new and distinct cultivar of pecan tree, substantially as herein illustrated and described.

* * * * *